(12) United States Patent
Valencia

(10) Patent No.: US 11,020,271 B2
(45) Date of Patent: Jun. 1, 2021

(54) VITRECTOMY PROBE WITH ROTATIONAL HELICAL CUTTER

(71) Applicant: Novartis AG, Basel (CH)

(72) Inventor: Salomon Valencia, Aliso Viejo, CA (US)

(73) Assignee: Alcon Inc., Fribourg (CH)

( * ) Notice: Subject to any disclaimer, the term of this patent is extended or adjusted under 35 U.S.C. 154(b) by 378 days.

(21) Appl. No.: 15/924,992

(22) Filed: Mar. 19, 2018

(65) Prior Publication Data

US 2018/0271705 A1  Sep. 27, 2018

Related U.S. Application Data

(60) Provisional application No. 62/477,360, filed on Mar. 27, 2017.

(51) Int. Cl.
| A61F 9/007 | (2006.01) |
| A61F 9/013 | (2006.01) |
| A61B 17/00 | (2006.01) |
| A61B 17/3207 | (2006.01) |

(52) U.S. Cl.
CPC .. *A61F 9/00763* (2013.01); *A61B 17/320783* (2013.01); *A61B 2017/00544* (2013.01); *A61F 9/013* (2013.01)

(58) Field of Classification Search
CPC .. A61B 17/320783; A61B 2017/00544; A61B 17/3207; A61B 17/320016; A61F 9/00763; A61F 9/013; A61F 9/00754
See application file for complete search history.

(56) References Cited

U.S. PATENT DOCUMENTS

| 4,530,356 A | 7/1985 | Helfgott et al. |
| 5,019,035 A | 5/1991 | Missirlian |
| 5,176,628 A | 1/1993 | Charles |
| 9,517,161 B2 | 12/2016 | Underwood |
| 9,615,969 B2 | 4/2017 | Nissan |
| 9,693,898 B2 | 7/2017 | Farley |
| 10,555,834 B2 | 2/2020 | Charles |
| 2008/0154292 A1* | 6/2008 | Huculak ............. A61F 9/00763 606/167 |
| 2012/0221033 A1 | 8/2012 | Auld et al. |
| 2014/0296900 A1 | 10/2014 | Barnes et al. |

(Continued)

OTHER PUBLICATIONS

Charles, S., Fluidics and Cutter Dynamics, Physics matter in deciding on cut rates and duty cycles, Retinal Physician, Apr. 1, 2012, pp. 58-60, vol. 9.

(Continued)

*Primary Examiner* — Shaun L David
*Assistant Examiner* — Christina C Lauer

(57) ABSTRACT

Vitrectomy probes and methods related thereto are disclosed herein. The disclosure describes various example vitrectomy probes having a rotational helical cutter. An example helical cutter includes an outer cutter portion and an inner cutter portion received therewithin. The inner cutter portion is operable to rotationally reciprocate within the outer cutter portion about a longitudinal axis thereof. A helical shearing surface formed at a distal end of the inner cutter portion is operable to sever material entering the cutter via a port formed in the outer cutter portion.

15 Claims, 8 Drawing Sheets

(56) References Cited

U.S. PATENT DOCUMENTS

| | | | |
|---|---|---|---|
| 2015/0327881 A1* | 11/2015 | Willhite et al. | ............................ A61B 17/320783 606/180 |
| 2017/0071788 A1 | 3/2017 | Anderson | |
| 2017/0333252 A1 | 11/2017 | Biancalana et al. | |
| 2018/0104101 A1 | 4/2018 | Lopez | |
| 2019/0038460 A1* | 2/2019 | Peterson | ............. A61F 9/00763 |
| 2019/0314201 A1 | 10/2019 | Paydar | |

OTHER PUBLICATIONS

Dugel, P. U., MD. (Feb. 2009). Early Clincal Experience With the Constellation Vision System. Safety is always a top priority, but increased efficiency is a critical benefit for the ASC. Retinal Physician. Retrieved Mar. 1, 2018, from https://www.retinalphysician.com/supplements/2009/february-2009/special-edition/.

* cited by examiner

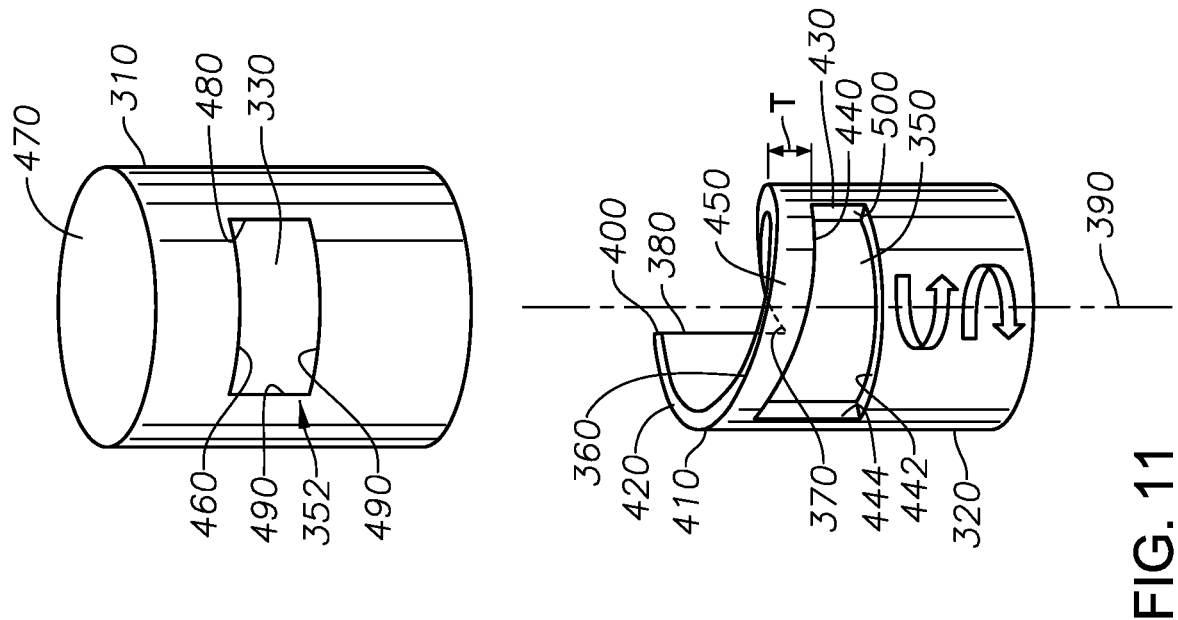
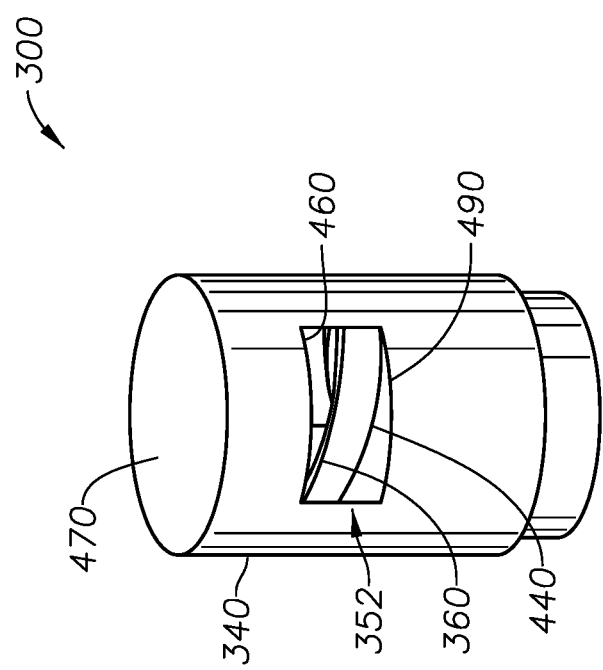
FIG. 10
FIG. 11

VITRECTOMY PROBE WITH ROTATIONAL HELICAL CUTTER

CROSS-REFERENCE TO RELATED APPLICATIONS

This application claims the benefit of U.S. Provisional Application No. 62/477,360, filed Mar. 27, 2017, the entire contents of which are incorporated by reference.

TECHNICAL FIELD

The present disclosure relates to an ophthalmic microsurgical instrument. Particularly, the present disclosure is directed to a vitreoretinal surgical instrument, e.g., a vitrectomy probe, having a rotational helical cutter.

BACKGROUND

Vitrectomy probes are used during vitreoretinal surgery to remove ocular tissues, such as vitreous humor and membranes covering the retina. These probes have a port for drawing in and dissecting tissues. As the port opens, tissue is drawn into the port. As the port closes, the incarcerated tissue is severed by the cutter and removed.

SUMMARY

According to one aspect, the disclosure describes a vitrectomy probe that includes a handle and a cutter extending longitudinally along a longitudinal axis from a distal end of the handle. The cutter includes an outer cutting portion coupled to the handle and an inner cutting portion received within the first lumen and rotatable within the outer cutter portion about the longitudinal axis. The outer cutter portion includes a cylindrical member defining a first lumen; and a first port formed proximate to a distal end of the outer cutter portion. The inner cutter portion includes a cylindrical member defining a second lumen and a distal end comprising a first helical shearing edge extending around at least a portion of the circumference of the distal end. The second lumen may be in fluid communication with the first lumen. The inner cutter portion is rotatable in a first direction about the longitudinal axis such that the helical shearing edge is rotated past the first port to perform a shearing action.

Another aspect of the disclosure encompasses a method for actuating a vitrectomy probe that includes providing the cutter coupled to a distal end of the vitrectomy probe. The cutter includes an outer cutting portion coupled to the handle. The outer cutting portion includes a cylindrical member defining a first lumen and a first port formed proximate to a distal end of the outer cutter portion. The cutter also includes an inner cutting portion received within the first lumen and rotatable within the outer cutter portion about the longitudinal axis. The inner cutter portion includes a cylindrical member defining a second lumen. The second lumen is in fluid communication with the first lumen, and a distal end of the inner cutter portion includes a first helical shearing edge extending around at least a portion of the circumference of the distal end. The method also includes rotating the inner cutter portion in a first direction about the longitudinal axis such that the helical shearing edge is rotated past the first port to perform a shearing action.

The various aspects may include one or more of the following features. The first port includes a port shearing edge, and the port shearing edge and the first helical shearing edge cooperate to perform the shearing action. The inner cutter portion further includes a vertical edge parallel with the longitudinal axis. The first helical edge extends from a proximal end of the vertical edge. The inner cutter portion is rotatably reciprocal within the outer cutter portion in the first direction and a second direction opposite the first direction. The inner cutter portion is rotatable in the first direction by a first amount and rotatable in the second direction by the first amount. Rotation of the inner cutter portion in a first direction about the longitudinal axis to perform a shearing action corresponds to the inner cutter portion entirely occluding the first port. The first helical shearing edge extends along the distal end of the inner cutter portion less than 360°. The inner cutter portion also includes a second port. The second port is aligned with the first port when the inner cutter portion is at an end of rotation of the inner cutter portion in the first direction.

The various aspects may also include one or more of the following features. The first port includes a first port shearing edge and a second port shearing edge. The second port includes a second helical shearing edge, and the first port shearing edge cooperates with the first helical shearing edge to sever material extending through the first port when the inner cutter portion rotates in the first direction. The second port shearing edge cooperates with the second helical shearing edge to sever material extending through the aligned first port and second port when the inner cutter portion rotates in the second direction. A width of the second port is the same or larger than a width of the first port. The second helical shearing edge parallels the first helical shearing edge. The outer cutter portion includes a distal end surface oriented perpendicular to the longitudinal axis. The outer cutter portion includes a distal end surface that is disposed at an angle relative to the longitudinal axis. An actuator mechanism is operable to rotatably reciprocate the inner cutter portion. The actuator mechanism includes one of an electric motor, a pneumatic actuator, or hydraulic actuator.

The various aspects may also include one or more of the following features. A rotational direction of the inner cutter portion is reversed when the inner cutter portion is stopped rotating in the first direction. The inner cutter portion is rotatable in the first direction by a first amount and is rotatable in the second direction by the first amount. The inner cutter portion includes a second port. The second port is aligned with the first port when the inner cutter portion is at an end of rotation of the inner cutter portion in the first direction. The first port includes a first port shearing edge and a second port shearing edge. The second port includes a second helical shearing edge. The first port shearing edge cooperates with the first helical shearing edge to sever material extending through the first port when the inner cutter portion rotates in the first direction, and the second port shearing edge cooperates with the second helical shearing edge to sever material extending through the aligned first port and second port when the inner cutter portion rotates in the second direction.

The details of one or more implementations of the present disclosure are set forth in the accompanying drawings and the description below. Other features, objects, and advantages will be apparent from the description and drawings, and from the claims.

DESCRIPTION OF DRAWINGS

FIG. 10 shows a distal end of another example rotational helical cutter having a dual port configuration.

FIG. 11 is an exploded view of the cutter shown in FIG. 10.

DETAILED DISCLOSURE

Figure 1:
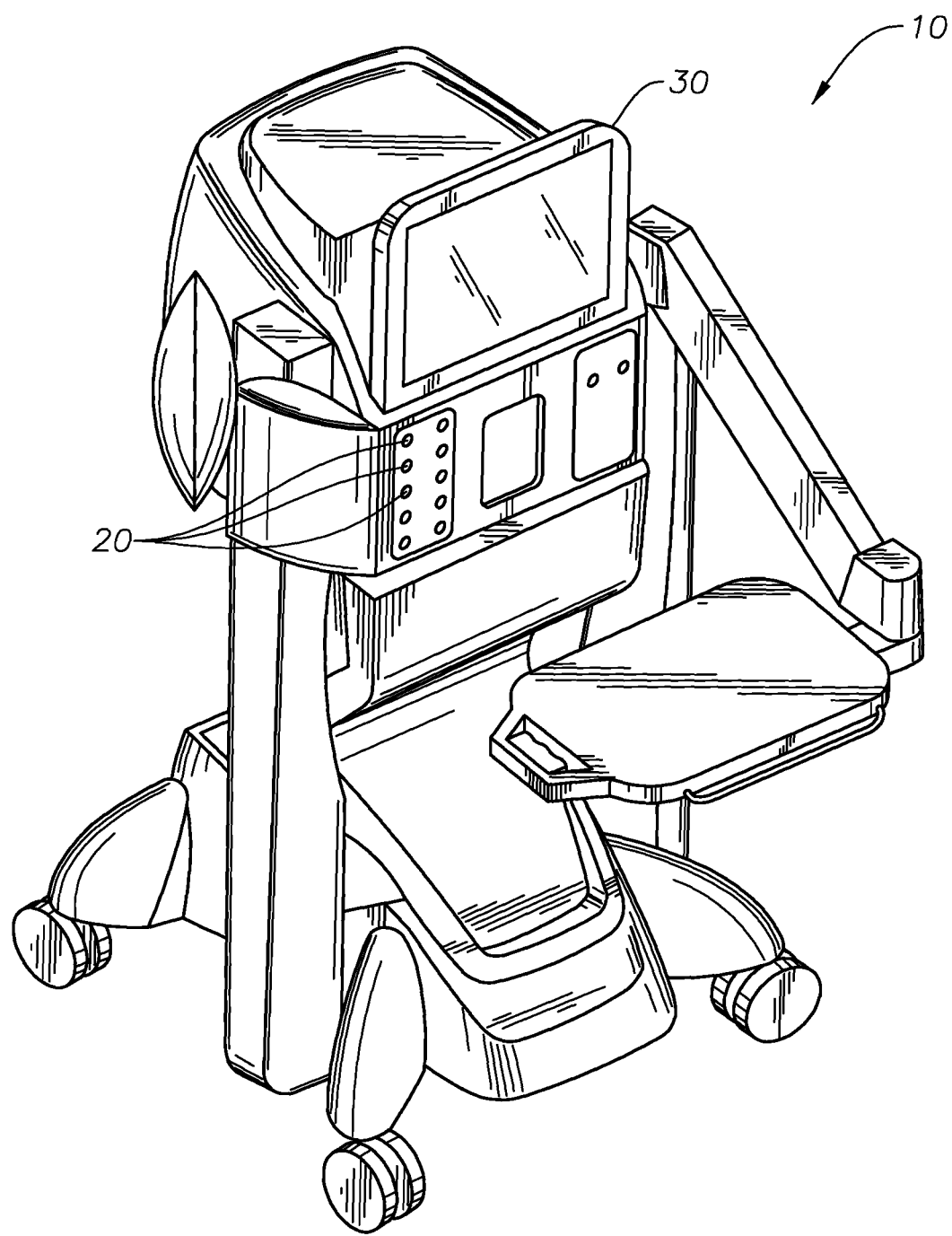
FIG. 1 shows an example surgical console.

For the purposes of promoting an understanding of the principles of the present disclosure, reference will now be made to the implementations illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one implementation may be combined with the features, components, and/or steps described with respect to other implementations of the present disclosure.

The present disclose describes microsurgical instruments having a rotational guillotine-type cutter in which the inner cutter has a helical cutting surface. The microsurgical instruments include vitrectomy probes that include a cutter having an outer cutter portion or needle and an inner cutter portion. The inner cutter portion is disposed within the needle and is rotatable therein. In the context of a vitrectomy probe, the cutter is used to perform a vitrectomy procedure in which vitreous humor (interchangeably referred to as "vitreous") is severed and removed from the eye in order to gain access to the retina of the eye. Upon completion of the vitrectomy, other surgical procedures, such as procedures to correct a problem with the retina may be accomplished. In contrast with an axial type guillotine vitrectomy probes that have a tendency to reflux fluid due to the axial reciprocal action of the inner cutter portion, rotational guillotine-type cutters do not include such a fluid reflux tendency such vitrectomy probes do not include an axial reciprocal action. Rather, the inner cutter portion of a rotational guillotine-type vitrectomy probes rotates about a longitudinal axis.

Additionally, because the inner cutter portion of the rotational guillotine-type cutters as described herein do not longitudinally move towards a distal end of the cutter, there is a lower risk that the inner cutter portion would make contact with a distal end of the outer cutter portion. Further, the port formed in the outer cutter portion may be placed closer to the distal end of the cutter, providing the cutter with a closer end cutting capability. That is, such cutters are able to cut more closely to the retina.

Although the following discussion is made in the context of ophthalmology, the scope of the disclosure is not so limited. Rather, the apparatuses, systems, and methods described herein may be applicable to numerous other fields, both inside and outside the medical arts.

FIG. 1 shows an example surgical console (interchangeably referred to as "console") 10 within the scope of the present disclosure. The surgical console may be a vitreoretinal surgical console, such as the Constellation® surgical console produced by Alcon Laboratories, Inc., 6201 South Freeway, Fort Worth, Tex. 76134 U.S.A. The console 10 may include one or more ports 20. One or more of the ports 20 may be utilized for providing infusion and/or irrigation fluids to the eye or for aspirating materials from the eye. One or more of the ports 20 may also be used to provide power, such as electrical or pneumatic power, to an instrument connected to the console 10. The console 10 may also include a display 30 for interfacing with the console 10, such as to establish or change one or more operations of the console 10. In some instances, the display 30 may include a touch-sensitive screen for interacting with the console 10 by touching the screen of the display 30. A probe, such as a vitrectomy probe may be coupled to a port 20 for dissecting ocular tissues and aspirating the ocular tissues from the eye.

Figure 2:
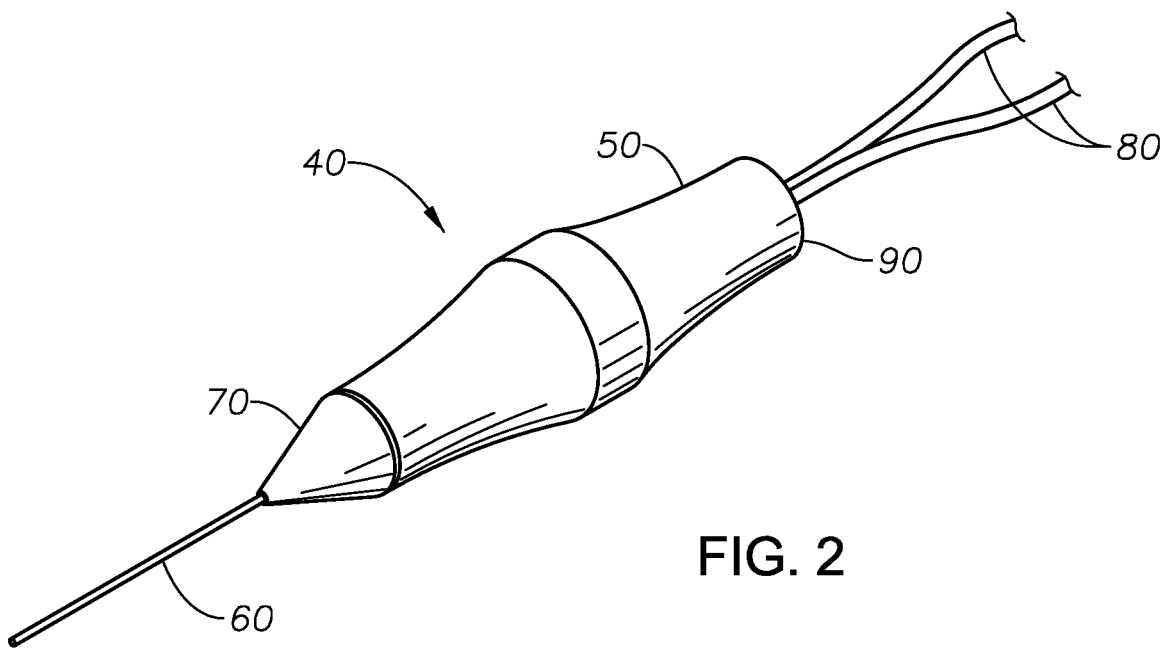
FIG. 2 shows an example vitrectomy probe having a cutter with a rotational helical cutter.

FIG. 2 shows an example vitrectomy probe 40. The vitrectomy probe 40 includes a handle 50 that is sized and shaped to fit into a hand of a user, such as a surgeon, and a cutter 60 extending from a distal end 70 of the handle 20. The vitrectomy probe 10 may also include one or more conduits 80 extending from a proximal end 90 of the handle 50. One of the conduits 80 may be an aspiration line that is operable to conduct material, such as fluid, tissue, and other material, from the eye. One or more of the conduits 80 may be a power cord to provide electrical power to the vitrectomy probe 40. For example, in instances where the cutter 60, described in more detail below, is operated by an electric motor, a conduit 80 connects the electric motor to a power supply in order to power the operation of the cutter 60. In other instances, one or more conduits 80 may be included that convey pneumatic pressure to a vitrectomy probe 40 that utilizes pneumatic pressure to operate the cutter 60. Further, other types of actuator mechanisms may be used to operate the cutter 60. Thus, the cutter may be operated electrically, pneumatically, hydraulically, mechanically, or in any other manner. Although two conduits 80 are shown in FIG. 1, it is within the scope of the disclosure that additional or fewer conduits 80 may be used.

The mechanism used to actuate the cutter 60 may be a single acting mechanism or a double acting mechanism. In a single acting mechanism, a force applied by the cutter operating mechanism moves the inner cutter portion in a first direction while a return spring returns the inner cutter portion to its initial position. In a dual acting mechanism, the cutter operating mechanism moves the inner cutter portion both in a first direction and returns the inner cutter portion to its initial position. A pneumatic diaphragm in which pneumatic pressure is applied to both sides of the diaphragm to oscillate the inner cutting portion is an example of a dual acting mechanism.

Figure 3:
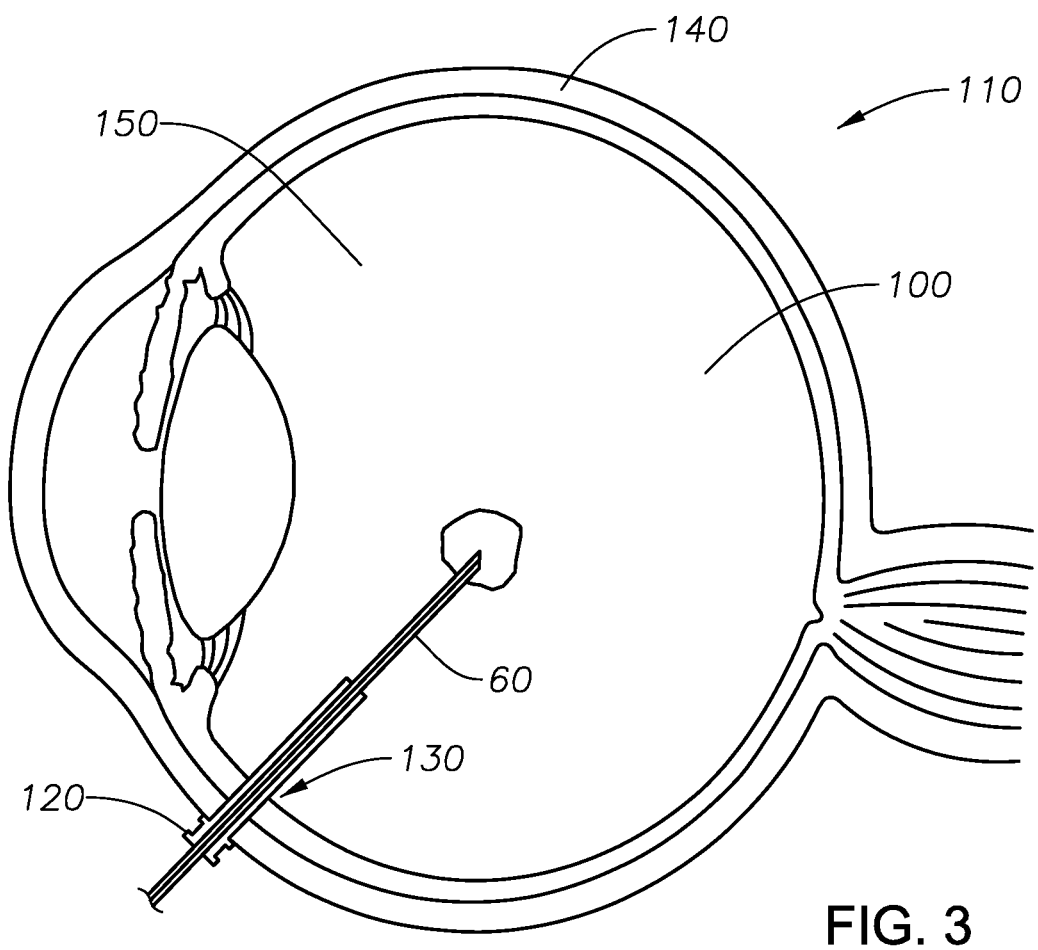
FIG. 3 shows a cross-sectional view of an eye in which a cutter of a vitrectomy probe extends into a posterior segment of the eye.

As illustrated in FIG. 3, during an ophthalmic surgical procedure, such as a retinal surgical procedure, the cutter 60 is inserted into the posterior segment 100 of the eye 1100, such as through a cannula 120 disposed in an incision 130 through the sclera 140 of the eye 110, to remove and aspirate ocular tissues. For example, during a retinal surgical procedure, the cutter 60 may be inserted into the posterior chamber 100 of the eye 110 to remove vitreous 150, a transparent jelly-like substance that occupies the volume defined by the posterior segment 100. The cutter 60 may also be used to remove membranes covering the retina or other tissues.

Figure 4:
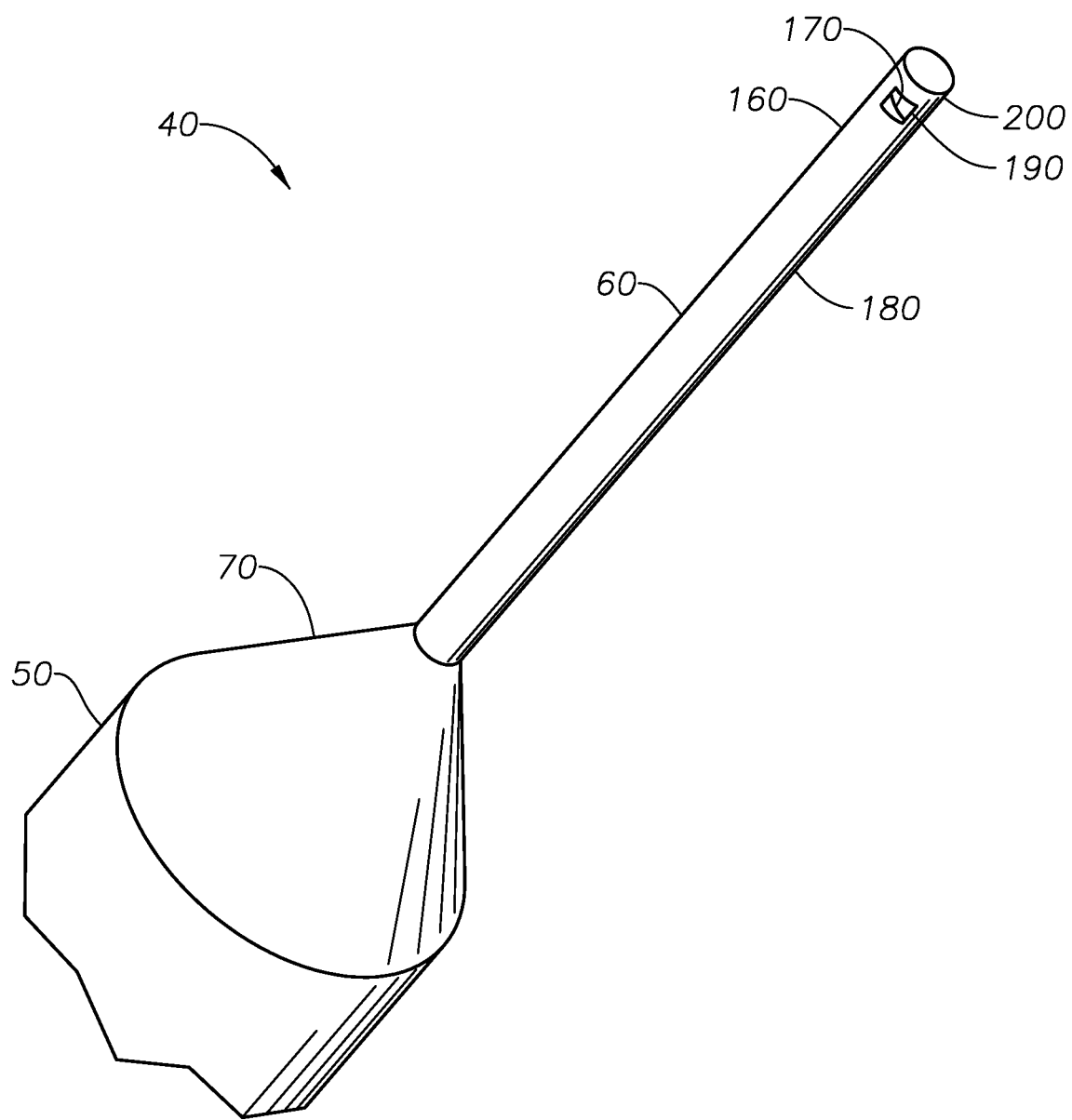
FIG. 4 shows a detail view of a distal end of an example vitrectomy probe that includes a rotational helical cutter.

FIG. 4 shows a detail view of an example vitrectomy probe 40. The cutter 60 includes an outer cutter portion 160 and an inner cutter portion 170. In the illustrated example, the outer cutter portion 160 is an elongated cylindrical tube that terminates with an end surface 270, and the inner cutter portion 170 is an elongated cylindrical tube that is open at both ends. In other implementations, the outer cutter portion 160 and the inner cutter portion 170 may have a different configuration. The outer cutter portion 160 includes a lumen 162 (shown in FIG. 6, for example) and defines an exterior surface 180 of the vitrectomy probe 40. The inner cutter portion 170 also includes a lumen 172. The inner cutter portion 170 is received within the lumen 162 of the outer cutter portion 160 and is moveable within the outer cutter portion 160. Particularly, the inner cutter portion 170 is rotatable within the outer cutter portion 160. The lumen 162 and the lumen 172 combine to form part of an aspiration passage 174 (shown, for example, in FIG. 7) used to convey material out of the eye. In some implementations, the aspiration passage 174 fluidly communicates with a conduit 80, as shown in FIG. 2, through which the aspirated material is removed from the vitrectomy probe 40. That is, a fluid, such as a gas or liquid, is movable between the aspiration passage 174 and the conduit 80. The outer cutter portion 160 includes a port 190 formed at a distal end 200 of the cutter 60 through which material, such as vitreous, is drawn into the cutter 60. The port 190 is in fluid communication with the lumen 162. The outer cutter portion 160 is coupled to and otherwise fixed relative to the handle 50. The inner cutter portion 170 is movable relative to the outer cutter portion 160. The port 190 is illustrated has being generally rectangular in shape. However, the port 190 may have other shapes. For example, the port 190 may have an elliptical or oval shape, a triangular shape, a square shape, or any other desired shape. The port 190 may extend about the circumference of the outer cutter portion 160 by, for example, 50°, 55°, 60°, 65°, 70°, 75°, 80°, 85°, 90°, 95°, 100°, 105°, 110°, 115°, 120°, or any other angle greater than or less than the indicated range or any amount between the values indicated.

Figure 6:
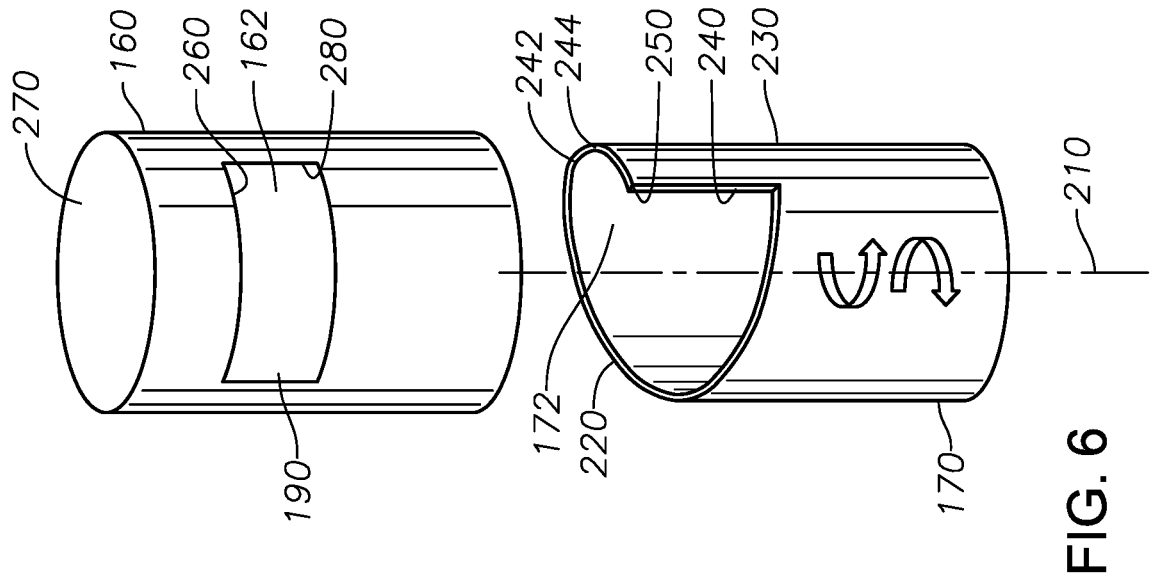
FIG. 6 is an exploded view of the cutter shown in FIG. 5.
Figure 5:
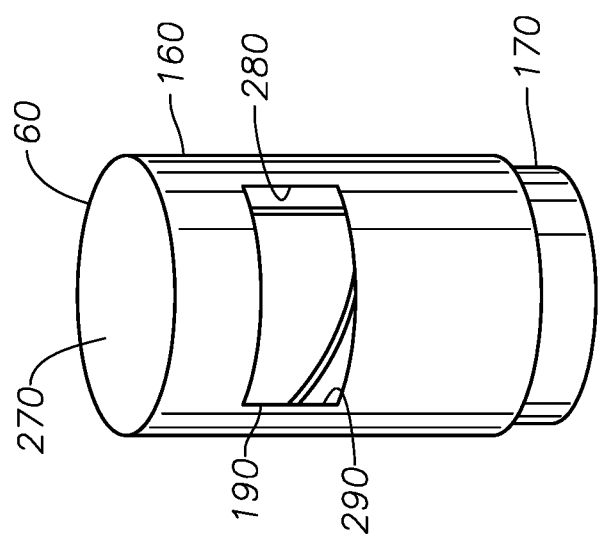
FIG. 5 shows a distal end of an example rotational helical cutter.

FIG. 5 shows a detail view of the distal end 200 of the cutter 60. FIG. 6 is an exploded view of the distal end 200 of the cutter 60 shown in FIG. 5. The inner cutter portion 160 and the outer cutter portion 170 are coaxially arranged about longitudinal axis 210 of the cutter 60. The longitudinal axis 210 also defines a rotational axis about which the inner cutter portion 170 rotates relative to the outer cutter portion 180.

Referring to FIG. 6, the inner cutter portion 170 includes a helical shearing edge 220. The helical shearing edge 220 is an inclined plane that wraps about the longitudinal axis 210. The helical shearing edge 220 begins at a first end 230 of an edge 240. The helix angle of the helical shearing edge 220 may be any desired helix angle. The helix angle may be measured as an angle the helical shearing edge 220 forms with a plane perpendicular to the longitudinal axis 210. In some instances, the helix angle of the helical shearing edge 220 may be selected such that rotation of the inner cutter portion 170, from an initial starting position where the port 190 is in a fully open condition, by 180° or less is operable to fully occlude port 190. In some implementations, the helix angle of the helical shearing edge 220 is selected to be approximately 10° to 30°, such that, from a fully open condition, the port 190 is made to become fully closed after rotation of the inner cutter portion 170 by 110°, 120°, 130°, 140°, 150°, 160°, 170°, 180°, 190°, 200°, 210°, 210°, 230°, 240°, 250°, 260°, 270°, 280°, 290°, 300°, or any other desired angle of rotation either larger or smaller than the indicated values or between the indicated values. While in some implementations, the helix angle of the helical edge portion 220 may be within a range of 10° to 30°, the scope is not so limited. Rather, the helix angle may be greater than or less than the recited range. Thus, the helix angle of the helical shearing edge 220 may vary to any other desired value. For example, the helix angle of the helical shearing edge 220 may be vary based on a longitudinal length of the port 190, lateral size of the port 190 (i.e., the angular span of the port 190 across the circumference of the inner cutter portion 170), an amount of rotation of the inner cutter portion 170 at which the port 190 become fully closed or occluded by the inner cutter portion 170, which correspond to the port 190 and helical shearing edge 220 cooperating to perform a complete shearing action. Thus, in some implementations, where fully occlusion of the port 190 is desired after only a short angular rotation of the inner cutter portion 170, the helix angle of the helical shearing edge 220 may be steep, such as, for example, an angle towards the larger end of the angular range of 0° to 90°. In other instances, such as where the complete shearing action may be desirable to take place over a large angular rotation of the inner cutter portion 170, the helix angle of the helical shearing edge 220 may be more shallow. For example, the angle may be towards the lower end of the 0° to 90° angular range. Thus, it is within the scope of the present disclosure that the helix angle of the helical edge portion 220 may be any desired angle that is operable to cut material extending into the port 190 over a rotation of 360° or less of the time the inner cutter portion 170.

For a given angular speed, reducing the angular rotation of the inner cutter portion 170 needed to fully close the port 190 reduces a total amount of time needed to cycle the port from a fully open condition to a fully closed condition. By reduces the cycle time of the cutter 60, cutting and removal of material is made to occur more rapidly, thereby having the potential to decrease a total time of a surgical procedure. In some implementations, the angular rotation in each direction of rotation may be approximately 110° to 140°. However, the scope of the disclosure is not so limited. Rather, the angular rotation amount of the inner cutter portion 170 may vary to less than or greater than the indicated range and may vary based on other aspects of the cutter 60, such as the size of the port 190, the pitch of the helical shearing edge 220, etc.

Edge 240 is illustrated as a vertical edge that extends parallel with the longitudinal axis 210. However, in other implementations, the edge 240 may also be sloped to define a helical surface. In some implementations, the helix angle of the edge 240 may be formed at a different angle from that of the helical shearing edge 220. In some instances, the helical shearing edge 220 may terminate at a second end 250 of the edge 240. However, in other implementations, the helix angle of the helical shearing edge 220 may terminate along the circumference of the inner cutter portion 170 at a location other than at the second end 250 of the edge 240, as shown, for example, in FIG. 6. FIG. 6 shows the helical shearing edge 220 terminating at a location 242. Thereafter, in the illustrated example, a remaining edge 244 of the inner cutter portion 170 is disposed in a plane that is perpendicular to the longitudinal axis 210. In other implementations, the remaining edge 244 may not be in a plane that is perpendicular to the longitudinal axis 210. Thus, in some implementations, the remaining edge 244 may be sloped to form a helical edge having a helix angle. The helix angle of the remaining edge 244 may be different than the helix angle of the helical shearing edge 220.

Figure 7:
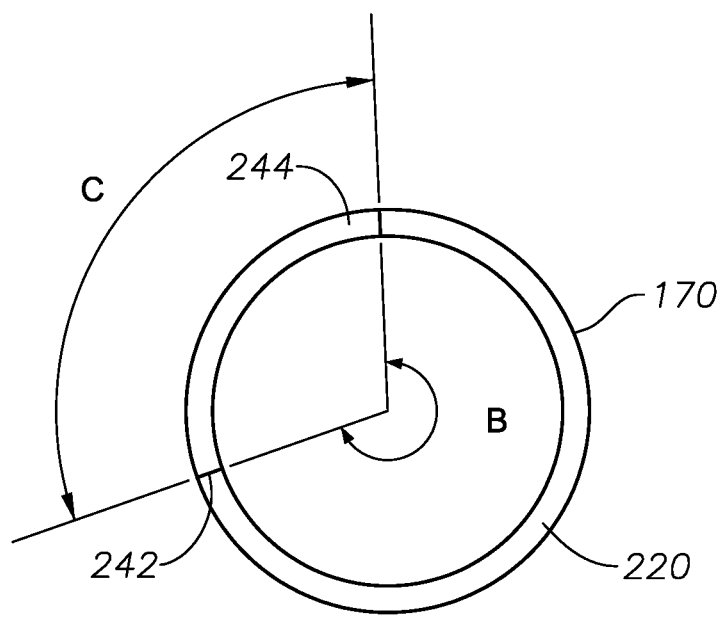
FIG. 7 is a top view of an example inner cutter portion.

FIG. 7 shows a top view of the inner cutter portion 170. As shown, the helical shearing edge 220 angularly extends about the longitudinal axis 210 by an angle B, starting from the edge 240 and terminating at the location 242. The angle B may be within a range of 300 to 360°. In some instances, the angle B may be 300°, 305°, 310°, 315°, 320°, 325°, 330°, 335°, 340°, 345°, 350°, 355°, or 360°. In still other instances, the angle B may be less than the indicated values or an angular value between the indicated angles. However, for reasons already explained above, the angles B and C may vary depending, for example, on the angle of rotation of the of the inner cutter portion 170 to cause a complete shearing action, a size of the port 190, etc. The edge portion 244 angularly extends about longitudinal axis 210 by an angle C. The angle C extending from location 242 to the edge 240 may be within a range of 0° to 60°. In some instances, the angle C may be 0°, 5°, 10°, 15°, 20°, 25°, 30°, 35°, 40°, 45°, 50°, 55°, °, 325°, 330°, 335°, 340°, 345°, 350°, 355°, or 360°. In still other instances, the angle B may be less than the indicated values or an angular value between the indicated angles. The edge portion 244 may define a surface that is perpendicular to the longitudinal axis 210. In some implementations, the edge portion 244 may be eliminated where the helical shearing edge 220 extends entirely around the distal edge of the inner cutter portion 170.

Figure 8:
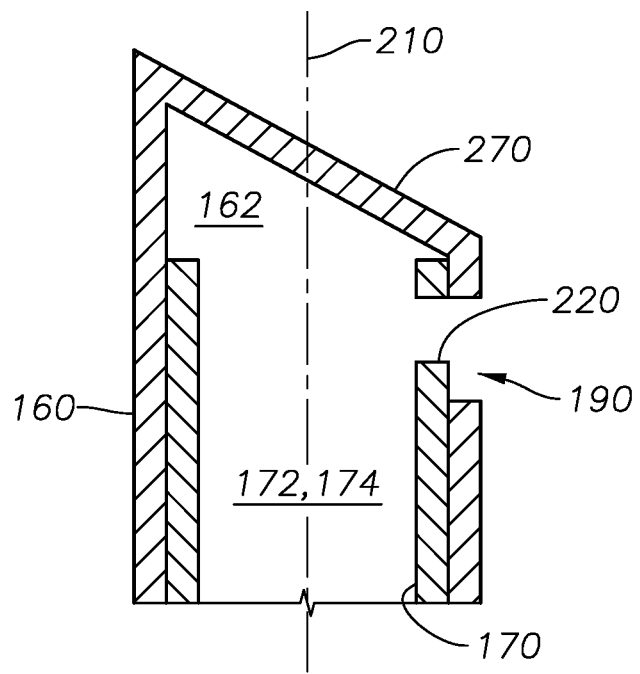
FIG. 8 is a longitudinal cross-sectional view of another example cutter.

As described in more detail below, the helical shearing edge 220 defines a shearing edge that works in combination with a port shearing edge 260 defined by a distal edge of the port 190 to sever vitreous that extends into the cutter 60 through the port 190. Additionally, the cutter 60 is shown has having a distal surface 270 that is perpendicular to the longitudinal axis 210. However, the scope of the disclosure is not so limited. Rather, in other implementations, the distal surface 270 may be beveled. FIG. 8 is a cross-sectional side view of another example cutter 60 showing a beveled distal surface 270. The beveled distal surface 270 permits the port 190 to be brought closer to ocular tissues, such as the retina, in order to remove additional material that may otherwise be unreachable with a cutter 60 having a distal surface 270 that is perpendicular to the longitudinal axis 210. In some implementations, the angle of the beveled distal surface 270 relative to a plane perpendicular to the longitudinal axis 210 may be in the range of 10° to 60°. For example, in some instances, the angle of the beveled distal surface 270 may be 10°, 15°, 20°, 25°, 30°, 35°, 40°, 45°, 50°, 55°, 60°, or any other desired angle.

Figure 9:
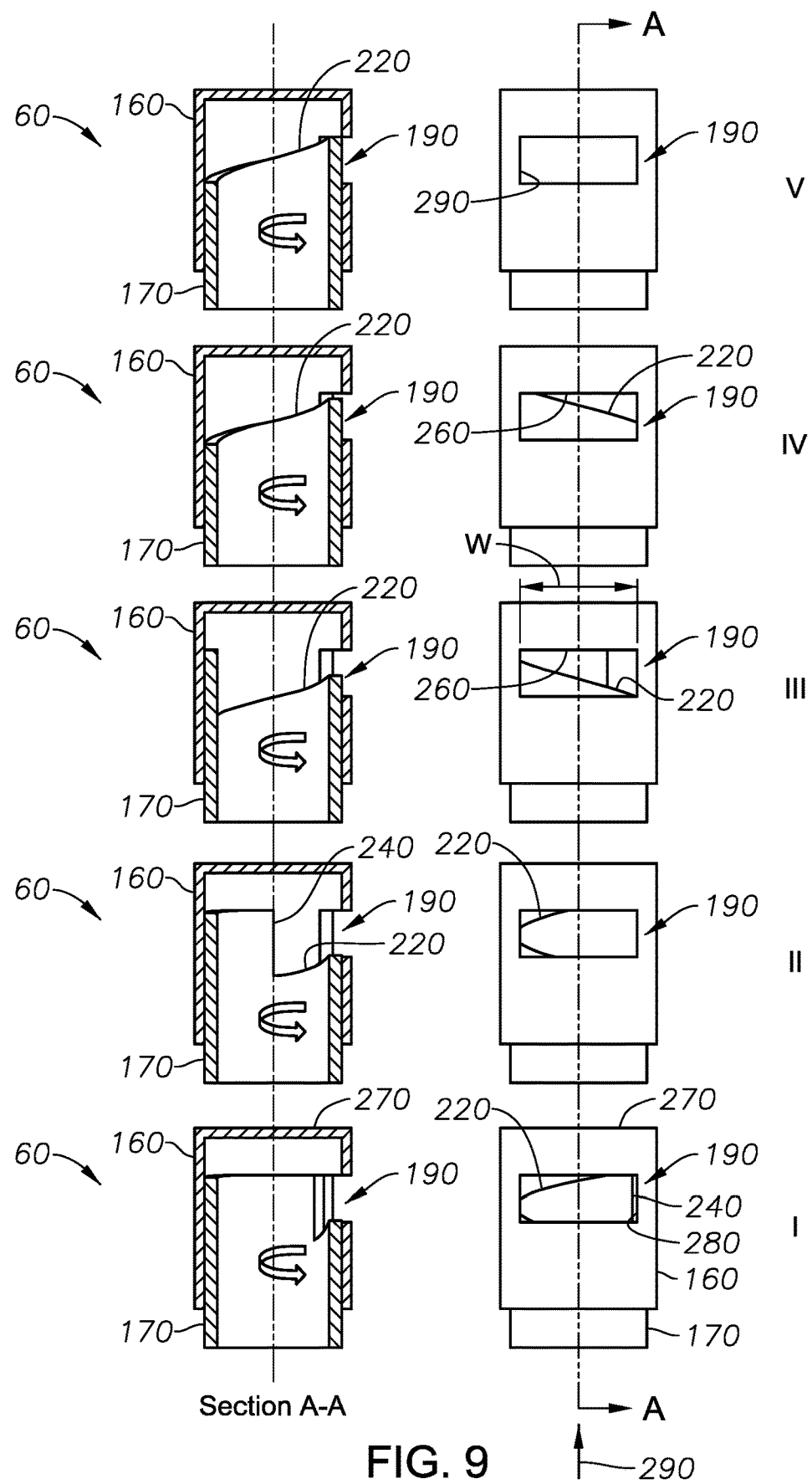
FIG. 9 is a series of images showing operation of a rotational helical cutter.

FIG. 9 illustrates operation of an example cutter 60 within the scope of the disclosure. In operation a cutter actuation mechanism, for example, housed within the handle 50, actuates the inner cutter portion 170 to rotate about longitudinal axis 210. Particularly, FIG. 9 is a series of images showing a position of the inner cutting portion 170 relative to the outer cutting portion 160 as the inner cutter portion 170 is rotated relative to the outer cutter portion 160. At each position indicated, a side view of the cutter 60 taken along line A-A is show directly adjacent.

At position I shown in the lower portion of FIG. 9, the port 190 is in a fully open condition. In the fully open condition, the edge 240 of the inner cutter portion 170 aligns with a side edge 280 of the port 190. In a first motion corresponding to a clockwise direction when viewing the cutter from a direction of arrow 290, the inner cutter portion 170 is rotated. In the illustrated example, each of the rotation of the inner cutter portion 170 represented by the different positions shown in FIG. 9 may be 27.5°. However, this amount of angular rotation is provided merely as an example to illustrate closing of the port 190 as the inner cutter portion 170 is rotated about the longitudinal axis 210.

At position II, the inner cutter portion 170 has been rotated an angular amount. As a result, due to the helical shearing edge 220 of the inner cutter portion 170, the port 190 begins to become occluded. As a result, at position II, rotation of the inner cutter portion 170 has caused the port 190 to begin to close. A portion of the helical shearing edge 220 is visible on a left lower corner of the port 190, as viewed in FIG. 9.

At position III, the inner cutter portion 170 has, again, been partially rotated about the longitudinal axis 210. At this position of the inner cutter portion 170, the port 170 is shown as being fifty percent open, the helical shearing edge 220 extending across an entire width W of the port 190. At this position, the helical shearing edge 220 is nearing the port shearing edge 260. At position IV, the helical shearing edge 220 has begun to pass the port shearing edge 260, which would cause material, such as vitreous, extending through the port 190 to be cut. At position IV, a portion of the port 190 remains unobstructed. Thus, at position IV, the port 190 remains partially open. Position V shows the port 190 fully closed as the inner cutter portion 170 fully obstructs the port 190.

In the example illustrated, from position I to position V, the inner cutter portion 170 has rotated 180° less an angular amount corresponding to the opening size of port 190. At the fully closed condition of port 190 shown in FIG. 9 at position V, the edge 240 aligns with a side edge 290 of the port 190 opposite the side edge 280. Therefore, in some implementations, the port 190 may extend over an angle of 60° to 80°, resulting in a total rotation of the inner cutter port of, for example, 110° to 140° from position I to position V.

With the port 190 fully closed, rotation of the inner cutter portion 170 is reversed. As the inner cutter portion 170 is rotated in a clockwise direction (as seen when viewing the cutter 60 in the direction of arrow 290), the port 190 opens. Opening of the port 190 follows the same series of images shown in FIG. 9 when viewed in reverse order from position V to position I. The inner cutter portion 170 is rotated until the inner cutter portion 170 is returned to its initial position, shown at position I.

The inner cutter portion 170 may be reciprocated rotationally about the longitudinal axis 210 at a rate of, for example, 5,000 cycles, 10,000 cycles, 15,000 cycles, 20,000 cycles, 40,000 cycles, or any other desired rate of operation. A cycle is defined as an oscillatory movement, i.e., movement of the inner cutter portion 170 in a first angular direction from an initial position to a first position and movement of the inner cutter portion 170 from the first position back to the initial portion in a second angular direction opposite the first direction. A point at which the inner cutter portion 170 stops rotating in the first rotational direction and reverses in the second rotational direction may correspond to full closure of the port 190. The operational rate or frequency of the cutter 60 may be referred to as a cutting rate, because the frequency of the inner cutter portion 170 corresponds to the number of cuts the cutter 60 is capable of making, since the cutter 60 is able to make a single cut per cycle of the inner cutter portion 170.

However, FIGS. 10 and 11 show another example cutter 300 included with another example vitrectomy probe. The concepts associated with the cutter 60, described above, are also applicable to the cutter 300 described below. Similar to cutter 60, the cutter 300 has an outer cutter portion 310 and an inner cutter portion 320 which may be similar to outer cutter portion 160 and inner cutter portion 170, respectively. The outer cutter portion 310 includes a lumen 330 and defines an exterior surface 340 of the vitrectomy probe, which may be similar to vitrectomy probe 40. The inner cutter portion 320 also includes a lumen 350. The inner cutter portion 320 is received within the lumen 330 of the outer cutter portion 310 and is moveable within the outer cutter portion 310 in a manner similar to that described above with respect to the cutter 60. Particularly, the inner cutter portion 320 is rotatable within the outer cutter portion 310. The lumen 330 and the lumen 350 combine to form part of an aspiration passage (similar to the aspiration passage 174 shown in FIG. 7) that is used to convey material out of the eye. The outer cutter portion 310 includes a port 352 formed at a distal end of the cutter 300 through which material, such as vitreous, is drawn into the cutter 300. The port 352 is in fluid communication with the lumen 330. The outer cutter portion 310 is coupled to and otherwise fixed relative to a handle of the vitrectomy probe, which may be similar to the handle 50. The inner cutter portion 320 is movable relative to the outer cutter portion 310. Similar to the port 190, the port 352 may have a rectangular shape, an oval or elliptical shape, a square shape, a triangular shape, or any other desired shape. Further, the port 352 may extend about the circumference of the inner cutter portion 320 by, for example, 50°, 55°, 60°, 65°, 70°, 75°, 80°, 85°, 90°, 95°, 100°, 105°, 110°, 115°, 120°, or any other angle greater than or less than the indicated range or any amount between the values indicated.

The inner cutter portion 320 also includes a helical shearing edge 360. Similar helical shearing edge 220, the helical shearing edge 360 is an inclined plane that wraps about the longitudinal axis 390. The helical shearing edge 360 begins at a first end 370 of an edge 380. The helix angle of the helical shearing edge 220 may be any desired helix angle. In some instances, the helix angle of the helical shearing edge 360 may be selected such that rotation of the inner cutter portion 320, from an initial starting position where the port 352 is in a fully open condition, by 180° or less is operable to fully occlude port 352. In one example implementation, the helix angle of the helical shearing edge 360 is selected to be 10°, such that, from a fully open condition, the port 352 is made to become fully closed by a 300° rotation of the inner cutter portion 320. In other implementations, the helix angle of the helical shearing edge 360 may be within a range of 10° to 30°. However, as explained above in the context of cutter 60, the helix angle of the helical shearing edge 360 may be selected to be any angle, particularly any angle between 0° and 90°, and the helix angle may be selected based on other aspects of the cutter 300, such as, for example, a longitudinal length of the port 352, lateral size of the port 352 (i.e., the angular span of the port 352 across the circumference of the inner cutter portion 320), an amount of rotation of the inner cutter portion 320 at which the helical shearing edge 360 has extended distally past the entire port shearing edge 460 of the port 352, thereby resulting in a complete shearing action. Thus, in some implementations, where it is desired to have the helical shearing edge 360 distally past the port shearing edge 460 after only a short angular rotation of the inner cutter portion 320, the helix angle of the helical shearing edge 360 may be steep, such as an angle towards the upper end of the angular range of 0° to 90°. In other instances, such as where the complete shearing action may be desirable to take place over a large angular rotation of the inner cutter portion 320, the helix angle of the helical shearing edge 360 may be more shallow. For example, the angle may be towards the lower end of the 0° to 90° angular range. Thus, it is within the scope of the present disclosure that the helix angle of the helical edge portion 360 may be any desired angle that is operable to cut material extending into the port 352 over a rotation of 360° or less of the time the inner cutter portion 320.

For a given angular speed, reducing the angular rotation of the inner cutter portion 320 needed to fully close the port 352 reduces a total amount of time needed to cycle the port 352 from a fully open condition to a fully closed condition. By reduces the cycle time of the cutter 300, cutting and removal of material is made to occur more rapidly, thereby having the potential to decrease a total time of a surgical procedure.

Figure 12:
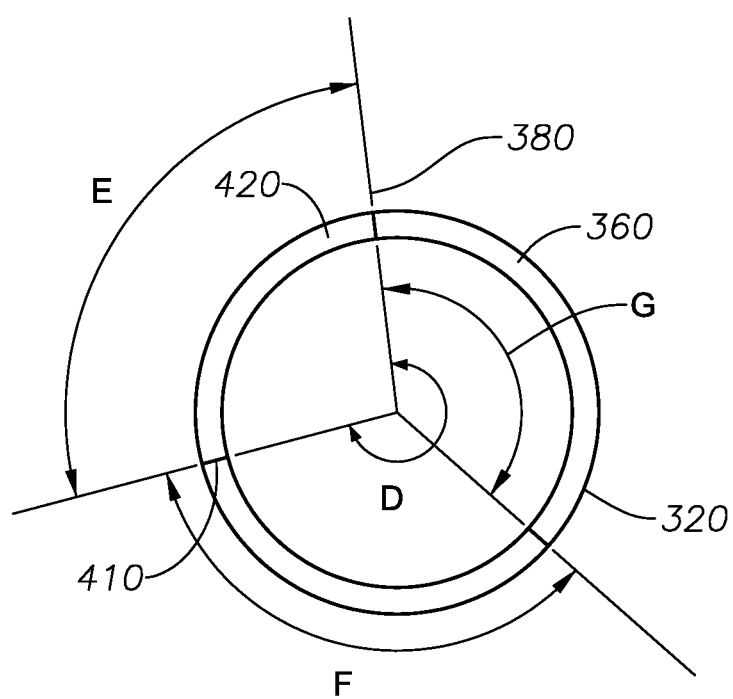
FIG. 12 is a top view of another example inner cutter portion.

Edge 380 is illustrated as a vertical edge that extends parallel with longitudinal axis 390. However, in other implementations, the edge 380 may also be sloped to define a helical surface. In some implementations, the angle of the edge 380 may be from that of the helical shearing edge 360. In some instances, the helical edge 380 may terminate at a second end 400 of the helical shearing edge 360. However, in other implementations, the helix angle of the helical shearing edge 360 may terminate along the circumference of the inner cutter portion 320 at a location other than at the second end 400 of the edge 380, as shown, for example, in FIG. 11. FIG. 12 is a top view of the inner cutter portion 320. As shown in FIG. 12, the helical shearing edge 360 angularly extends about the longitudinal axis 390 by an angle D, starting from the edge 380 and terminating at location 410. The angle D may be within the range of 300 to 360°. In some instances, the angle D may be 300°, 305°, 310°, 315°, 320°, 325°, 330°, 335°, 340°, 345°, 350°, 355°, or 360°. In still other instances, the angle D may be less than the indicated range or an angular value between the indicated values. An edge portion 420 angularly extends about the longitudinal axis 390 by an angle E, extending from location 410 to the edge 380. The angle E may be within a range of 0° to 60°. In some instances, the angle E may be 0°, 5°, 10°, 15°, 20°, 25°, 30°, 35°, 40°, 45°, 50°, 55°, °, 325°, 330°, 335°, 340°, 345°, 350°, 355°, or 360°. In still other instances, the angle E may be less than the indicated range or an angular value between the indicated values. The edge portion 420 may define a surface that is perpendicular to the longitudinal axis 390. In some implementations, the edge portion 420 may be eliminated where the helical shearing edge 360 extends entirely around the distal edge of the inner cutter portion 320. The angle G is an angle extending from the edge 380 to circumferential location where the port 430 begins. In some implementations, the angle G may be within the range of 200° to 240°. For example, the angle G may be 200°, 205°, 210°, 215°, 220°, 225°, 230°, 235°, and 240°. Further, the angle G may be selected to be larger or smaller than the indicated range or any angle between the recited values. Angle F corresponds to the angular size of the port 430 measured about the longitudinal axis 390. The angle F may be within a range of 80° to 100°. For example, the angle G may be 80°, 85°, 90°, 95°, or 100°. Further, the angle F may be selected to be larger or smaller than the indicated range or any angle between the recited values. In some instances, the port 430 ends at a location where the helical shearing edge 360 ends. In some instances, the helical shearing edge 360 ends after extending about the longitudinal axis less than 360°. In such instances, the edge portion 420 extends from a location where the helical shearing edge 360 ends and terminates at the edge 380. The surface defined by the edge portion 420 may have a pitch different from the helical shearing edge 360. In some instances, the edge portion 420 defines a surface that may be perpendicular to the longitudinal axis 390.

Similar to the helical shearing edge 220, the helical shearing edge 360 defines a shearing edge that works in combination with the port shearing edge 460 defined by a distal edge of the port 352 to sever vitreous that extends into the cutter 300 through the port 352. Additionally, the cutter 300 is shown has having a distal surface 470 that is perpendicular to the longitudinal axis 210. However, similar to the distal surface 270, the distal surface 470 may be beveled in a manner similar to that illustrated in FIG. 8. A beveled distal surface permits the port 352 to be brought closer to ocular tissues, such as the retina, in order to remove additional material that may otherwise be unreachable with a cutter 300 having a distal surface 470 that is perpendicular to the longitudinal axis 390.

Unlike the inner cutter portion 170, the inner cutter portion 320 also includes a port 430 that is in fluid communication with the lumen 350. The port 430 is defined by a helical shearing edge 440 at a distal end, a proximal edge 442, a first lateral side 444, and a second lateral side 500. The helical shearing edge 440 that extends parallel with the helical shearing edge 360. That is, the helical shearing edge 440 extends at a helix angle that corresponds to the same helix angle of the helical shearing edge 360. A helical strip 450 is defined between the helical shearing edge 440 and the helical shearing edge 360. The strip 450 has a thickness T. The thickness T is measured in a direction parallel to the longitudinal axis 390. In some instances, a thickness, T, of the strip 450 may be within the range of 0.004 inches to 0.008 inches. However, the thickness T may be selected to be any desired thickness.

An angular amount over which the port 430 extends about the longitudinal axis 390 is indicated by angle G, as shown in FIG. 12. This dimension of the port 430 may be referred to as the lateral size of the port 430. In the illustrated example, the lateral size of the port 430 is the same as the lateral size of the port 352. Thus, in some implementations, when the inner cutter portion 320 has reach an end of its rotational movement in a first direction, the ports 352 and 430 align such that the port 352 is in a fully open condition. Similarly, in such instances, a length of the side edge 480 is the same as a length of a side edge 500 of the port 430. However, the scope of the disclosure is not so limited. In other implementations, the lateral size of the port 430 may be larger or smaller than the lateral size of the port 352. In other instances, the length of the side edge 480 may be different than the length of the side edge 500. For example, in some implementations, the length of the side edge 480 may be larger than the length of the side edge 500. In other implementations, a length of the side edge 480 may be smaller than the length of the side edge 500.

Operation of the cutter 300 is similar to that of cutter 60. The inner cutter portion 320 is reciprocally rotated within the outer cutter portion 310 by a defined angular amount. That is, the inner cutter portion 320 is operable to rotate in a reciprocal manner within the outer cutter portion 310 about the longitudinal axis 390. With the port 352 is a fully open condition, operation of the cutter 300 behaves the same as the cutter 60 and, as such, FIG. 9 is applicable to operation of the cutter 300 in this respect.

With the cutter 300 in a fully open condition, the edge 380 may be aligned with a side edge 480 of the port 352. In a manner similar to that illustrated in FIG. 9, as the inner cutter port 320 rotates clockwise as the inner cutter member is viewed along arrow 290, the helical shearing edge 360 progressively moves across the port 352 where the helical shearing edge 360 cooperates with the port shearing edge 460 to shear vitreous or other material that extends through the port 352. However, as the inner cutter portion 320 rotates clockwise such that the shearing edge 360 has moved distally across the port 352 by an amount T, corresponding to the thickness of strip 450, the port 352 begins to reopen as the port 430 formed in the inner cutter portion 320 begins to overlap the port 352 formed in the outer cutter portion 310. As the ports 352 and 430 begin to overlap, providing communication with the lumen 350, additional vitreous is able to enter the cutter through the aligned ports 352 and 430.

When the inner cutter portion 320 has reached the end of rotation in the clockwise direction, the port 430 fully aligns with the port 352 such that the port 352 is in the fully open condition. In the illustrated example, the port 430 is sized such that alignment with the port 352 results in the port 352 being completely unobstructed. In other instances, the port 430 may be sized such that alignment with port 352 results in only a partial opening of the port 352. That is, in some instances, alignment of the port 430 and the port 352 when the inner cutter portion 320 has reached an end of rotation in the clockwise direction results in the port 352 being partially obstructed by the inner cutter portion 320.

The inner cutter portion 320 reverses and begins moving in a counterclockwise direction, as viewed from arrow 290 in FIG. 9. As the inner cutter portion 320 returns to its initial starting position, the vitreous that has entered through the aligned ports 352 and 430 is severed by cooperation between the helical shearing edge 440 and a port shearing edge 490. Further, as inner cutter portion 320 returns to its initial starting position, the helical shearing edge 360 moves proximally relative to the port 352, thereby reopening the port 352 and allowing vitreous to reenter. Consequently, when the inner cutter portion 320 reverses once again, the cutting behavior repeats. As a result of the port 430 formed in the inner cutter portion 320, the cutter performs two cuts over a single cutting cycle, thereby doubling the cutting rate of the cutter 300.

It should be understood that, although many aspects have been described herein, some implementations may include all of the features, while others may include some features while omitting others. That is, various implementations may include one, some, or all of the features described herein.

Persons of ordinary skill in the art will appreciate that the examples encompassed by the present disclosure are not limited to the particular implementations described above. In that regard, although illustrative implementations have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A vitrectomy probe comprising:
    a handle;
    a cutter extending longitudinally along a longitudinal axis from a distal end of the handle, the cutter comprising:
        an outer cutter portion coupled to the handle, the outer cutter portion comprising:
            a cylindrical member defining a first lumen; and
            a first port formed proximate to a distal end of the outer cutter portion; and an inner cutter portion received within the first lumen and rotatable within the outer cutter portion about the longitudinal axis, the inner cutter portion comprising:
a cylindrical member defining a second lumen, the second lumen in fluid communication with the first lumen;
an open distal end comprising a first helical shearing edge extending around at least a portion of a circumference of the open distal end, the inner cutter portion rotatable in a first direction about the longitudinal axis such that at least a portion of the helical shearing edge is rotated past the first port to perform a shearing action,
wherein the inner cutter portion further comprises a second port formed in a wall of the inner cutter portion and circumscribed by the inner cutter portion;
wherein the first port comprises a first port shearing edge and a second port shearing edge, wherein the second port comprises a second helical shearing edge, wherein the first port shearing edge cooperates with the first helical shearing edge to sever material extending through the first port when the inner cutter portion rotates in the first direction, and wherein the second port shearing edge cooperates with the second helical shearing edge to sever material extending through the first port and second port when the inner cutter portion rotates in a second direction opposite the first direction.

2. The vitrectomy probe of claim 1, wherein the inner cutter portion further comprises a vertical edge parallel with the longitudinal axis, the first helical edge extending from a proximal end of the vertical edge.

3. The vitrectomy probe of claim 2, wherein the inner cutter portion is reciprocably rotated within the outer cutter portion in the first direction and a second direction opposite the first direction.

4. The vitrectomy probe of claim 3, wherein the inner cutter portion is rotatable in the first direction by a first amount and is rotatable in the second direction by the first amount.

5. The vitrectomy probe of claim 1, wherein rotation of the inner cutter portion in a first direction about the longitudinal axis to perform a shearing action corresponds to the inner cutter portion entirely occluding the first port.

6. The vitrectomy probe of claim 1, wherein the first helical shearing edge extends along the distal end of the inner cutter portion less than 360°.

7. The vitrectomy probe of claim 1, wherein a width of the second port is the same or larger than a width of the first port.

8. The vitrectomy probe of claim 1, wherein the second helical shearing edge parallels the first helical shearing edge.

9. The vitrectomy probe of claim 1, wherein the outer cutter portion further comprises a distal end surface oriented perpendicular to the longitudinal axis.

10. The vitrectomy probe of claim 1, wherein the outer cutter portion further comprises a distal end surface that is disposed at an angle relative to the longitudinal axis.

11. The vitrectomy probe of claim 1 further comprising an actuator mechanism operable to rotatably reciprocate the inner cutter portion.

12. The vitrectomy probe of claim 11, wherein the actuator mechanism comprises one of an electric motor, a pneumatic actuator, or hydraulic actuator.

13. A method for actuating a cutter of a vitrectomy probe, the method comprising:
providing the cutter coupled to a distal end of the vitrectomy probe, the cutter comprising:
an outer cutter portion coupled to the handle, the outer cutter portion comprising:
a cylindrical member defining a first lumen; and
a first port formed proximate to a distal end of the outer cutter portion; and
an inner cutter portion received within the first lumen and rotatable within the outer cutter portion about a longitudinal axis, the inner cutter portion comprising:
a cylindrical member defining a second lumen, the second lumen in fluid communication with the first lumen; and
an open distal end comprising a first helical shearing edge extending around at least a portion of a circumference of the open distal end, and
rotating the inner cutter portion through a first angular rotation amount in a first direction about the longitudinal axis such that at least a portion of the helical shearing edge is rotated past the first port to perform a shearing action;
reversing a rotational direction of the inner cutter portion when the inner cutter portion is stopped rotating in the first direction;
rotating the inner cutter portion through the first angular rotation amount in a second direction, opposite the first direction, about the longitudinal axis.

14. The method of claim 13, wherein the inner cutter portion further comprises a second port formed in a wall of the inner cutter portion and circumscribed by the inner cutter portion, the second port aligned with the first port when the inner cutter portion is at an end of rotation of the inner cutter portion in the first direction.

15. The method of claim 14, wherein the first port comprises a first port shearing edge and a second port shearing edge, wherein the second port comprises a second helical shearing edge, wherein the first port shearing edge cooperates with the first helical shearing edge to sever material extending through the first port when the inner cutter portion rotates in the first direction, and wherein the second port shearing edge cooperates with the second helical shearing edge to sever material extending through the aligned first port and second port when the inner cutter portion rotates in the second direction.

* * * * *